United States Patent
Williams et al.

(10) Patent No.: US 10,130,602 B2
(45) Date of Patent: Nov. 20, 2018

(54) USE OF L-CARNITINE, SALTS AND DERIVATIVES THEREOF FOR REDUCING OR PREVENTING FATIGUE AND IMPROVING COGNITIVE FUNCTION

(75) Inventors: Adriana Williams, Riehen (CH); Frauke Warrikoff, Frankfurt (DE); Ulla Freitas, Lorrach (DE); Richard Sasse, Bavel (NL); Kevin Owen, Canyon, TX (US)

(73) Assignee: Lonza Ltd., Visp (CH)

( * ) Notice: Subject to any disclaimer, the term of this patent is extended or adjusted under 35 U.S.C. 154(b) by 2 days.

(21) Appl. No.: 14/009,470

(22) PCT Filed: Apr. 4, 2012

(86) PCT No.: PCT/EP2012/056151
§ 371 (c)(1),
(2), (4) Date: Oct. 8, 2013

(87) PCT Pub. No.: WO2012/136699
PCT Pub. Date: Oct. 11, 2012

(65) Prior Publication Data
US 2014/0107201 A1    Apr. 17, 2014

Related U.S. Application Data
(60) Provisional application No. 61/479,653, filed on Apr. 27, 2011.

(30) Foreign Application Priority Data

Apr. 5, 2011 (EP) .................................... 11002833
Apr. 27, 2011 (EP) .................................... 11003448

(51) Int. Cl.
A61K 31/205    (2006.01)
(52) U.S. Cl.
CPC ................................... A61K 31/205 (2013.01)
(58) Field of Classification Search
CPC ..................................................... A61K 31/205
See application file for complete search history.

(56) References Cited

U.S. PATENT DOCUMENTS

| | | | | |
|---|---|---|---|---|
| 5,073,376 A | * | 12/1991 | Kohl et al. ..................... | 424/451 |
| 2007/0281010 A1 | * | 12/2007 | Reynolds ........................ | 424/464 |
| 2009/0297492 A1 | | 12/2009 | Satoh et al. | |

FOREIGN PATENT DOCUMENTS

| | | |
|---|---|---|
| JP | 2001517085 A | 10/2001 |
| JP | 2003135033 A | 5/2003 |
| JP | 2005097161 | 4/2005 |
| JP | 2005097161 A | 4/2005 |
| JP | 2006199666 A | 8/2006 |
| JP | 2007190029 A | 8/2007 |
| JP | 2007-233070 | 9/2007 |
| JP | 2007222128 A | 9/2007 |
| JP | 2008214338 A | 9/2008 |
| KR | 20030028328 A | 4/2003 |
| WO | 0243666 | 6/2002 |

OTHER PUBLICATIONS

Milgram et al. 2002, Neurobiology of Aging, vol. 23, pp. 737-745.*
Vermeulen et al. 2004, Psychosomatic Medicine, vol. 66, pp. 276-282.*
Rohde, 1999, Acetyl-L-carnitine and its effects on memory and cognition. National undergraduate research clearinghouse, 2.*
Goepp, Life Extension Magazine, Sep. 2006.*
Boksem et al., Effects of mental fatigue on attention: An ERP study, Cognitive Brain Research, vol. 25, pp. 107-116 (2005).
Cruciani et al., Safety, Tolerability and symptom outcomes associated with L-carnitine supplementation in patients with cancer, fatigue, and carnitine deficiency: A phase I/II study, Journal of Pain and Symptom Management, vol. 32, No. 5 (2006).
Dutta et al., L-carnitine supplementation attenuates intermittent hypoxia-induced oxidative stress and delays muscle fatigue in rats, Exp. Physiol., vol. 93 pp. 1139-1146 (2008).
Karlic et al., Supplementation of L-carnitine in athletes: Does it make sense?, Nutrition, vol. 20, pp. 709-715 (2004).
Kato et al., Mental fatigue and impaired response processes: Event-related brain potentials in a Go/NoGo task, Int'l Journal of Psychophysiology, vol. 72, pp. 204-211 (2009).
Kennedy et al., Improved cognitive performance and mental fatigue following a multi-vitamin and mineral supplemental with added guarana (*Paullinia cupana*), Appetite, vol. 50, pp. 506-513 (2008).
Kennedy et al., Monoterpenoid extract of sage (*Salvia lavandulaefolia*) with cholinesterase inhibiting properties improves cognitive performance and mood in healthy adults, Journal of Psychopharmacology, online http://jop.sagepub.com (2010).
Kennedy et al., A glucose-caffeine 'energy drink' ameliorates subjective and performance deficits during prolonged cognitive demand, Appetite, vol. 42, pp. 331-333 (2004).
Kobayashi et al., Acetyl-L-carnitine improves aged brain function, Geriatr Gerontol Int., vol. 10, pp. S99-S106 (2010).
Lorist et al., The influence of mental fatigue and motiviation on neural network dynamics; and EEG coherence study, Brain Research, vol. 1270, pp. 95-106 (2009).
Malaguarnera et al., L-carnitine treatment reduces severity of physical and mental fatigue and increases cognitive functions in centenarians: a randomized and controlled clinical trial 1-3, Am. J. Clin. Nutr., vol. 86, pp. 1738-1744 (2007).
Malaguarnera et al., Acetyl L-carnitine (ALC) treatment in elderly patients with fatigue, Archives of Gerontology and Geriatrics, vol. 46, pp. 181-190 (2008).
Montgomery et al., Meta-analysis of double blind randomized controlled clinical trials of acetyl-L-carnitine versus placebo in the treatment of mild cognitive impairment and mild Alzheimer's disease, Int'l Clinical Psychopharmacology, vol. 18, pp. 61-71 (2003).

(Continued)

Primary Examiner — Kara R McMillian
(74) Attorney, Agent, or Firm — Dority & Manning, P.A.

(57) ABSTRACT

The invention relates to the use of L-carnitine, a salt of L-carnitine, a derivative of L-carnitine and/or salt of a derivative of L-carnitine, as well as respective methods and compositions, for reducing or preventing fatigue and/or for improving cognitive function in an animal. The animal is preferably a healthy individual and the use is preferably a non-therapeutic use.

18 Claims, 9 Drawing Sheets

(56) References Cited

OTHER PUBLICATIONS

Figure 1:
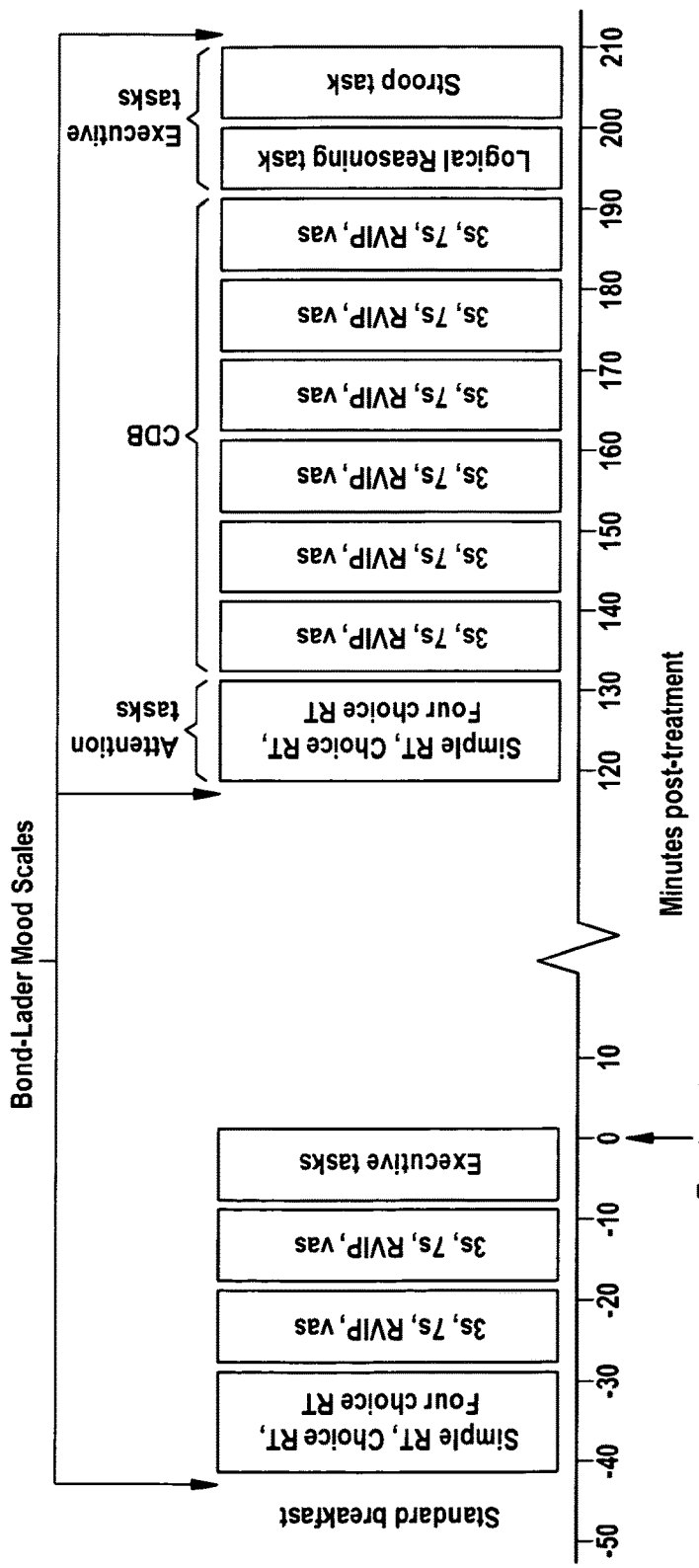

Reay et al., Single doses of Panax ginseng (G115) reduce blood glucose levels and improve cognitive performance during sustained mental activity, Journal of Psychopharmacology, vol. 19, pp. 357-365 (2005).

Reay et al., Effects of Panax ginseng, consumed with and without glucose, on blood glucose levels and cognitive performance during sustained 'mentally demanding tasks', Journal of Psychopharmacology, vol. 20, pp. 771 (2006).

Van der Linden, et al., Mental fatigue and the control of cognitive processes: effects on perseveration and planning, Acta Psychologica, vol. 113, pp. 45-65 (2003).

Malaguamera et al., L-Carnitine treatment reduces severity of physical and mental fatigue and increases cognitive functions in centenarians: a randomized and controlled clinical trial, Am. J. Clin. Nutr. 2007, 86: pp. 1738-1744.

Office Action dated Jul. 12, 2016 for the corresponding EP application EP12711673.9.

Benton et al., "The Influence on Cognition of the Interactions Between Lecithin, Carnitine and Carbohydrate", Psychopharmacology, 175, pp. 84-91; 2004.

Office Action dated Jan. 19, 2016 for the corresponding Japanese application JP2014-503128, Notice of Reasons for Rejection, pp. 1-3.

* cited by examiner

| Task Outcome | | Pre-dose | | Post-dose | | F | p |
|---|---|---|---|---|---|---|---|
| Simple Reaction Time (msec) | Placebo | 295 | 6.41 | 4.49 | 4.16 | 1.08 | 0.36 |
| | 500 LC | 294 | 9.18 | 0.53 | 5.67 | | |
| | 2000 LC | 296 | 7.51 | -0.42 | 6.14 | | |
| | 1000 ALC | 292 | 7.65 | 12.9 | 6.75 | | |
| Choice Reaction Time (% Correct) | Placebo | 96.5 | 0.72 | -1.10 | 0.76 | 2.05 | 0.12 |
| | 500 LC | 96.4 | 0.99 | -1.90 | 0.59 | | |
| | 2000 LC | 96.0 | 0.82 | 0.30 | 0.81 | | |
| | 1000 ALC | 96.3 | 0.67 | -0.50 | 0.48 | | |
| Choice Reaction Time (msec) | Placebo | 407 | 10.5 | -14.0 | 5.19 | 0.78 | 0.51 |
| | 500 LC | 433 | 32.7 | -32.7 | 35.9 | | |
| | 2000 LC | 402 | 8.85 | -9.81 | 4.89 | | |
| | 1000 ALC | 401 | 9.17 | 7.98 | 10.9 | | |
| 4- Choice Reaction Time (% Correct) | Placebo | 98.5 | 0.59 | -0.63 | 0.69 | 0.75 | 0.53 |
| | 500 LC | 98.8 | 0.35 | -0.10 | 0.49 | | |
| | 2000 LC | 98.9 | 0.38 | -1.15 | 0.68 | | |
| | 1000 ALC | 99.4 | 0.31 | -0.94 | 0.28 | | |
| 4-Choice Reaction Time (msec) | Placebo | 461 | 11.4 | 6.33 | 10.9 | 1.66 | 0.19 |
| | 500 LC | 473 | 14.3 | -17.4 | 8.52 | | |
| | 2000 LC | 462 | 11.9 | -3.32 | 10.0 | | |
| | 1000 ALC | 469 | 15.4 | 10.2 | 9.56 | | |
| Logical Reasoning (% Correct) | Placebo | 94.6 | 1.16 | -2.66 | 1.54 | 0.35 | 0.79 |
| | 500 LC | 93.4 | 1.40 | -3.02 | 2.05 | | |
| | 2000 LC | 94.0 | 1.48 | -0.82 | 1.44 | | |
| | 1000 ALC | 92.6 | 1.86 | -2.38 | 1.47 | | |
| Logical Reasoning Reaction Time (msecs) | Placebo | 3506 | 228 | -63.0 | 135 | 0.27 | 0.90 |
| | 500 LC | 3594 | 153 | -167 | 96.6 | | |
| | 2000 LC | 3478 | 194 | -59.4 | 80.3 | | |
| | 1000 ALC | 3543 | 153 | -47.8 | 89.9 | | |
| Stroop (% Correct) | Placebo | 97.2 | 0.47 | -0.10 | 0.49 | 0.56 | 0.64 |
| | 500 LC | 98.0 | 0.37 | -0.66 | 0.46 | | |
| | 2000 LC | 94.8 | 2.52 | -0.55 | 0.51 | | |
| | 1000 ALC | 97.8 | 0.44 | 0.12 | 0.43 | | |
| Stroop Reaction Time (msec) | Placebo | 625 | 24.2 | -14.5 | 14.1 | 0.88 | 0.46 |
| | 500 LC | 600 | 17.3 | 12.7 | 6.90 | | |
| | 2000 LC | 602 | 16.0 | 11.1 | 20.5 | | |
| | 1000 ALC | 626 | 20.0 | 9.60 | 12.7 | | |

Fig. 4

|  |  | Pre-dose | | Post-dose Repetition | | | | | | | |
|---|---|---|---|---|---|---|---|---|---|---|---|
|  |  |  |  | 1 | 2 | 3 | 4 | 5 | 6 | F | p |
| Serial 3s Total (Number) | Placebo | 57.3 | 3.12 | 4.05 | 1.58 | 0.32 | 1.58 | -0.79 | 1.84 | -2.37 | 2.56 | 0.79 | 1.89 | 0.63 | 2.18 | T=0.69 | 0.56 |
|  | 500 LC | 53.5 | 3.18 | 4.84 | 1.43 | 3.16 | 1.75 | 1.95 | 1.97 | 2.11 | 2.08 | 2.95 | 1.97 | 4.58 | 2.25 | TxR=0.46 | 0.96 |
|  | 2000 LC | 54.3 | 3.91 | 5.16 | 2.09 | 2.53 | 2.13 | 0.74 | 2.95 | 0.05 | 2.87 | 4.16 | 2.86 | 2.42 | 2.82 | | |
|  | 1000 ALC | 55.0 | 3.35 | 3.05 | 1.58 | 1.95 | 1.58 | 0.32 | 1.84 | -1.32 | 2.56 | 0.53 | 1.89 | 1.63 | 2.18 | | |
| Serial 3s Errors (Number) | Placebo | 1.95 | 0.43 | 0.79 | 0.40 | 0.05 | 0.47 | 0.79 | 0.37 | 0.63 | 0.54 | 0.47 | 0.81 | 0.16 | 0.38 | T=0.19 | 1.00 |
|  | 500 LC | 2.15 | 0.63 | 0.68 | 0.58 | 0.32 | 0.51 | 0.68 | 0.45 | 0.16 | 0.54 | 0.79 | 0.50 | 0.63 | 0.59 | TxR=0.16 | 0.93 |
|  | 2000 LC | 1.50 | 0.34 | 0.21 | 0.35 | 0.26 | 0.41 | 0.84 | 0.52 | 1.11 | 0.44 | 0.53 | 0.54 | 0.21 | 0.59 | | |
|  | 1000 ALC | 1.70 | 0.36 | 0.79 | 0.40 | 0.47 | 0.47 | 0.00 | 0.37 | 0.84 | 0.54 | 1.11 | 0.81 | 0.42 | 0.38 | | |
| Serial 7s Total (Number) | Placebo | 34.4 | 2.03 | 2.94 | 1.06 | 0.39 | 1.14 | 0.72 | 1.27 | 0.67 | 1.27 | 1.94 | 0.84 | 2.44 | 1.30 | T=0.95 | 0.42 |
|  | 500 LC | 34.1 | 2.43 | 2.28 | 0.99 | 3.22 | 1.08 | 2.67 | 1.13 | 4.00 | 1.81 | 4.11 | 1.97 | 3.06 | 1.14 | TxR=1.36 | 0.17 |
|  | 2000 LC | 34.2 | 1.91 | 3.28 | 1.24 | 0.72 | 1.29 | 2.72 | 2.33 | 3.39 | 1.55 | 0.61 | 1.05 | 3.22 | 1.67 | | |
|  | 1000 ALC | 35.0 | 2.24 | 1.11 | 1.06 | 1.61 | 1.14 | 0.22 | 1.27 | 0.28 | 1.27 | 3.11 | 0.84 | 3.61 | 1.30 | | |
| Serial 7s Errors (Number) | Placebo | 2.05 | 0.30 | -0.17 | 0.70 | 0.22 | 0.67 | 1.00 | 0.67 | 1.28 | 0.71 | 0.67 | 0.57 | 1.22 | 0.59 | T=0.67 | 0.58 |
|  | 500 LC | 1.95 | 0.43 | 0.22 | 0.53 | 0.28 | 0.48 | 0.56 | 0.62 | 0.89 | 0.60 | 0.94 | 0.83 | 0.44 | 0.34 | TxR=0.35 | 0.99 |
|  | 2000 LC | 1.95 | 0.42 | 0.61 | 0.61 | 0.78 | 0.63 | 1.00 | 0.98 | 1.06 | 0.72 | 1.06 | 0.60 | 1.61 | 0.72 | | |
|  | 1000 ALC | 2.40 | 0.61 | -0.28 | 0.70 | 0.11 | 0.67 | -0.11 | 0.67 | 0.28 | 0.71 | 0.83 | 0.57 | 0.39 | 0.59 | | |
| RVIP False Alarms (Number) | Placebo | 1.85 | 0.63 | -0.50 | 0.44 | 0.55 | 0.65 | 3.00 | 2.76 | -0.20 | 0.48 | -0.05 | 0.58 | -0.20 | 0.54 | T=0.30 | 0.82 |
|  | 500 LC | 2.15 | 0.65 | -0.75 | 0.62 | 1.20 | 1.28 | 2.05 | 2.45 | 0.75 | 1.02 | 0.90 | 0.85 | -0.35 | 0.47 | TxR=0.47 | 0.62 |
|  | 2000 LC | 1.30 | 0.29 | 0.20 | 0.51 | 1.25 | 0.77 | 1.10 | 0.72 | 0.40 | 0.44 | 0.15 | 0.42 | 1.10 | 0.69 | | |
|  | 1000 ALC | 1.90 | 0.51 | 0.00 | 0.63 | 1.30 | 0.65 | 2.40 | 1.88 | 1.40 | 1.08 | 1.25 | 1.00 | 0.10 | 0.38 | | |
| RVIP % Correct | Placebo | 51.3 | 4.44 | 9.50 | 3.71 | -2.38 | 3.72 | -3.38 | 3.76 | -5.88 | 2.99 | -3.25 | 3.39 | -5.13 | 3.50 | T=0.58 | 0.63 |
|  | 500 LC | 47.1 | 4.60 | 6.38 | 3.00 | 4.13 | 2.67 | 2.25 | 2.80 | -1.00 | 3.31 | -3.13 | 3.56 | -4.25 | 3.48 | TxR=1.12 | 0.34 |
|  | 2000 LC | 54.1 | 4.99 | 5.00 | 2.03 | -1.50 | 1.95 | -3.38 | 1.96 | -3.75 | 2.29 | -4.25 | 2.21 | -8.13 | 2.41 | | |
|  | 1000 ALC | 53.5 | 3.82 | 6.00 | 2.89 | -1.88 | 3.11 | -2.13 | 2.85 | -8.25 | 3.00 | -6.88 | 2.85 | -5.50 | 2.63 | | |
| RVIP Reaction Time (msecs) | Placebo | 490 | 9.30 | -10.5 | 8.79 | -1.28 | 5.45 | 11.5 | 13.2 | 5.12 | 6.18 | 8.03 | 8.39 | 1.86 | 7.89 | T=2.78 | 0.049 |
|  | 500 LC | 517 | 12.1 | -25.7 | 8.49 | -13.1 | 7.95 | -14.7 | 7.14 | -9.35 | 9.19 | -6.71 | 8.02 | -10.8 | 7.13 | TxR=0.86 | 0.62 |
|  | 2000 LC | 489 | 9.71 | -0.71 | 3.74 | 6.56 | 8.84 | 1.46 | 6.27 | 22.9 | 14.6 | 1.91 | 7.83 | 9.99 | 7.08 | | |

Fig. 5a

| Mental Fatigue (% along VAS) | | | | | | | | | | | | | | | |
|---|---|---|---|---|---|---|---|---|---|---|---|---|---|---|---|
| 1000 ALC | 498 | 7.98 | -11.5 | 6.08 | 12.3 | 11.1 | -2.08 | 6.98 | 1.12 | 8.80 | 14.8 | 9.41 | 12.9 | 9.45 | |
| Placebo | 55.0 | 3.55 | -5.75 | 2.35 | 0.75 | 2.98 | 5.75 | 2.61 | 9.40 | 2.07 | 9.25 | 2.32 | 10.5 | 2.74 | T=0.95 0.42 |
| 500 LC | 58.3 | 4.14 | -6.65 | 3.14 | -2.00 | 3.28 | 3.85 | 2.11 | 5.60 | 2.20 | 6.85 | 2.43 | 6.05 | 3.46 | TxR=0.61 0.86 |
| 2000 LC | 53.5 | 3.63 | -2.55 | 2.84 | 3.05 | 2.06 | 5.35 | 2.42 | 9.65 | 3.00 | 14.0 | 2.70 | 13.30 | 2.71 | |
| 1000 ALC | 55.2 | 4.08 | -3.90 | 3.10 | 3.25 | 3.52 | 6.85 | 3.95 | 8.95 | 2.98 | 12.2 | 3.23 | 12.80 | 3.12 | |

Fig. 5b

|  |  | Pre-dose | Post-dose 1 |  | Post-dose 2 |  | F |  | p |
|---|---|---|---|---|---|---|---|---|---|
| Alert | Placebo | 56.3 | 2.83 | 4.68 | 2.54 | -9.58 | 4.29 | T=1.60 | 0.20 |
|  | 500 LC | 57.2 | 2.74 | 4.08 | 2.19 | -8.34 | 3.46 | TxR=0.69 | 0.56 |
|  | 2000 LC | 57.9 | 2.46 | 4.40 | 1.99 | -10.8 | 3.76 |  |  |
|  | 1000 ALC | 58.1 | 2.92 | 1.42 | 2.49 | -14.7 | 3.7 |  |  |
| Content | Placebo | 61.3 | 2.49 | 4.40 | 2.14 | -4.18 | 3.38 | T=1.49 | 0.23 |
|  | 500 LC | 63.4 | 2.63 | 0.02 | 1.03 | -4.08 | 1.94 | TxR=1.63 | 0.19 |
|  | 2000 LC | 65.4 | 2.19 | 1.82 | 0.79 | -4.91 | 2.93 |  |  |
|  | 1000 ALC | 65.1 | 2.57 | -0.80 | 1.79 | -7.86 | 3.24 |  |  |
| Calm | Placebo | 61.5 | 2.89 | 0.10 | 3.21 | -5.90 | 4.67 | T=0.07 | 0.98 |
|  | 500 LC | 61.7 | 2.77 | -4.85 | 2.98 | -0.13 | 2.36 | TxR=4.48 | 0.007 |
|  | 2000 LC | 62.7 | 2.53 | -1.50 | 1.88 | -6.28 | 2.33 |  |  |
|  | 1000 ALC | 63.8 | 2.52 | -3.70 | 2.13 | -3.40 | 2.53 |  |  |

Fig. 6

USE OF L-CARNITINE, SALTS AND DERIVATIVES THEREOF FOR REDUCING OR PREVENTING FATIGUE AND IMPROVING COGNITIVE FUNCTION

The invention relates to uses of L-carnitine, a salt of L-carnitine, a derivative of L-carnitine and/or salt of a derivative of L-carnitine, and respective methods and compositions for reducing or preventing fatigue and/or for improving cognitive function in an animal.

BACKGROUND OF THE INVENTION

Carnitine (vitamin Bt; 3-hydroxy-4-trimethylammoniobutanoate) is a quaternary ammonium compound biosynthesized from the amino acids lysine and methionine. Carnitine exists in two stereoisomers. The biologically active form is L-carnitine, whilst its enantiomer, D-carnitine, is biologically inactive. L-carnitine (LC) is an endogenous compound, which plays a key metabolic role, transporting long chain fatty acids into the mitochondria for energetic oxidation. Supplementation with acetyl-L-carnitine (ALC) has been shown to increase overall regional cerebral metabolism in rodents. Carnitine and its esters also have non-metabolic roles in brain function as neuroprotectants, antioxidants and modulators of neurotransmission.

Carnitine deficiencies and chronic fatigue co-exist across a number of patient groups. Early evidence suggests that supplementation may improve indices of chronic fatigue associated with cancer (Cruciani et al. 2006). Evidence also suggests beneficial roles for supplementation with carnitine and its esters in attenuating the symptoms and cognitive deficits associated with Alzheimer's disease (Montgomery et al. 2003) and in reducing fatigue and improving cognitive function in centenarians (Malaguarnera et al., 2007, 2008).

Karlic and Lohninger suggest that carnitine supplementation may foster exercise performance of athletes. They conclude that there is evidence for a beneficial effect of L-carnitine supplementation in training, competition and recovery from strenuous exercise and in regenerative athletics.

JP 2005097161-A discloses an anti-fatigue composition for preventing physical and mental fatigue, which comprises coenzyme Q, carnitine and an inorganic acid as active ingredients.

Another fatigue improver based on biotin, carnitine and pantothenic acid as active ingredients is described in JP 07-233070-A.

A food supplement based on vitamin C, vitamin E, L-carnitine and alpha-lipoic acid for inhibiting the deterioration of cognitive function is disclosed in WO 02/43666 A2.

Therefore, L-carnitine is generally used in the art for the treatment of individuals suffering from diseases, such as cancer or Alzheimer's disease, or having an impaired metabolism as a result of high age or extreme physical exercise. Further, combinations of multiple active agents, comprising L-carnitine, have been suggested for other uses. Compositions for treating fatigue or improving cognitive function described in the art are mixed compositions comprising multiple active ingredients, such as vitamins and antioxidants.

PROBLEM UNDERLYING THE INVENTION

The problem underlying the invention is to provide a composition, or use or method, for reducing or preventing fatigue or for improving cognitive function in an animal, preferably a human animal. The composition shall overcome the above-mentioned problems and shall be applicable for healthy and young, or at least non-elderly, individuals. In other words, the fatigue or cognitive function shall not be the result of a disease, or associated with a disease, or with impaired metabolic function, for example due to high age. The composition shall be easily available, efficient and applicable without side effects in a simple manner.

DISCLOSURE OF THE INVENTION

Surprisingly, the problem underlying the invention is solved by the process according to the claims. Further inventive embodiments are disclosed throughout the description.

Subject of the invention is the use of L-carnitine, a salt of L-carnitine, a derivative of L-carnitine and/or a salt of a derivative of L-carnitine for reducing or preventing fatigue and/or for improving cognitive function in an animal.

L-carnitine is the physiologically active form of carnitine. In the following, the term "carnitine" refers to the active L-carnitine.

According to the invention, L-carnitine can be administered in the form of L-carnitine as such, a salt of L-carnitine, a derivative of L-carnitine and/or a salt of a derivative of L-carnitine, or mixtures thereof. In the following, when referring to administration modes and uses, the terms "L-carnitine" or "L-carnitine, a salt or derivative thereof" refer to "L-carnitine as such, a salt of L-carnitine, a derivative of L-carnitine and/or a salt of a derivative of L-carnitine".

Preferably, the inventive use is a non-therapeutic use. Preferably, the animal is a healthy animal. As used herein, "healthy" refers to the absence of illness or injury.

Preferably, the animal is human.

In a preferred embodiment of the invention, the use of L-carnitine is for improving cognitive function. Cognitive functions refer to higher brain functions that encompass sense, perception, recognition, judgment and action or suppression. Information on the surrounding circumstances is continuously transmitted via sense organs (visual sense, auditory sense, tactile sense, taste sense, and smell sense) to the brain, which selects the necessary information. At that time, the ability of a person to pay attention to a plurality of pieces of information (divided attention or allocated attention) is important. Selected pieces of information are integrated to form one piece of information having a particular meaning, that is, a perception. Next, perceived information is remembered for a short period of time, a current perception and a previous memory are checked against each other (recognition), and judgment is performed.

Cognitive performance can be evaluated by various measuring methods, for example, neuropsychologic tests and neurophysiological tests. Examples of such a neuropsychological test include a computerized Cognitive Demand Battery (CDB), CogHealth, Wechsler Adult Intelligence Scale, Stanford Binet Intelligence test, Visual Perception Test for Agnosia (VPTA), Standard Performance Test for Apraxia (SPTA), Wechsler Memory Scale-Revised, Clinical Assessment for Attention-Clinical Assessment for Spontaneity (CAT-CAS), Digit Cancellation Test for attention (D-CAT), Hamamatsu higher brain function scale, new Stroop test, Hasegawa dementia scale, Nishimura dementia scale, COG-NISTAT, multiphasic early dementia examination (MEDE), NS dementia test, TAIS, MMSE, and the like. Examples of such a neurophysiological test include event-related potentials, and the event-related potentials include contingent negative variation (CNV), P1-N1-P2, NA, Nd, N2b, P300, MMN, N400, and the like. In a more medical sense, evaluation is possible also by measuring the activity of high-level functions of the brain using functional magnetic resonance imaging (fMRI), single photon emission computed tomography (SPECT), optical topography, or the like. Furthermore, as a popular method, evaluation is possible also with so called "brain training (Nou-Tore)", which is a series of television game software. Moreover, such cognitive performance can be evaluated with, for example, measurements of physical fitness for checking the time taken to react to light.

In a preferred embodiment of the invention, the use of L-carnitine is for reducing or preventing physical fatigue. Physical fatigue or muscle weakness (or "lack of strength") is a direct term for the inability to exert force with one's muscles to the degree that would be expected given the individual's general physical fitness.

In another preferred embodiment of the invention, the use of L-carnitine is for reducing or preventing mental fatigue. Mental fatigue can manifest itself as somnolence (decreased wakefulness), or just as a general decrease of attention, not necessarily including sleepiness. It may also be described as a more or less decreased level of consciousness. In any case, this can be dangerous when performing tasks that require constant concentration, such as driving a vehicle. For instance, a person who is somnolent may experience microsleeps.

There are different ways to measure mental fatigue, e.g. by means of an EEG-based mental-fatigue monitoring system, self-rating fatigue scales, different standardized questionnaires, blink rate, or the Multidimensional Fatigue Inventory (MFI) which is a 20-item self-report instrument designed to measure fatigue. It covers the following dimensions: General Fatigue, Physical Fatigue, Mental Fatigue, Reduced Motivation and Reduced Activity. Preferably, the Cognitive Demand Battery test is used (CDB; Kennedy et al. 2008; Kennedy and Scholey 2004; Reay et al. 2005; 2006; Kennedy et al., 2010). The CDB-test is well established in the art.

Preferably, the animal is a healthy and/or young animal. So far, L-carnitine has not been associated with the improvement of mental and physical fatigue or cognitive function in healthy or young animals.

In a preferred embodiment of the invention, the animal, especially human individual, is not an elderly animal or individual. Preferably, the individual's age is below 60 or below 50. The individual may be an adult, or older than 8, 12, 16 or 18 years. Preferably, the age range is from 8 to 60 or from 16 to 50.

Preferably, the animal is a healthy animal. More preferably, the animal does not have decreased L-carnitine levels and/or impaired metabolic function as a result of a disease, or associated with a disease.

Preferably, the individual does not suffer from chronic fatigue and/or chronic L-carnitine depletion, dementia, cancer, neurodegenerative diseases, Alzheimer's disease, depression, age-related memory decline, bacterial or virus infections. Preferably, the impairment of cognitive function or fatigue is not due to the consumption of alcohol or other drugs known to impair such physical functions.

The fatigue, especially the physical fatigue, is preferably a result of working, such as mental work or light or medium physical work, or a result of mental stress, overstimulation, understimulation, jet lag, active recreation or lack of sleep. Preferably, the fatigue, especially the physical fatigue, is not a result of extreme physical exercise and/or the L-carnitine is not used in association with training, competition and recovery from extreme physical exercise of athletes.

In a preferred embodiment of the invention, the individual has a plasma level of L-carnitine, which is considered normal. L-Carnitine plasma levels are considered normal if they are >20 µmol/L. More importantly though is the ratio of esterified to free L-carnitine in plasma, as only the free L-Carnitine is active. Ratios of acyl-carnitine to free L-carnitine of >0.4 are considered to be related to L-Carnitine deficiency. According to the invention, it is preferred that the plasma ratio of acyl-carnitine to free L-carnitine of the individual is below 0.4.

In a preferred embodiment of the invention, before administration of the L-carnitine, salt or derivative thereof, the animal is experiencing a temporary fatigue and/or temporary impairment of cognitive function.

Preferably, the fatigue and/or impairment of cognitive function are a result of a prolonged time of mental exercise and/or lack of sleep. For example, a temporary fatigue and/or temporary impairment of cognitive function is experienced by students who study for a long time or by drivers, especially truck drivers, or by other individuals working on monotonous tasks for a long time without breaks.

In a preferred embodiment of the invention, the inventive use is for improving cognitive function of an animal, preferably a human, which is experiencing fatigue. In this embodiment, the animal may have impaired cognitive function associated with or resulting from fatigue. Thus the inventive use improves cognitive function of an animal experiencing fatigue.

In another preferred embodiment of the invention, the inventive use is for improving cognitive function of an animal, preferably human, which is not experiencing fatigue. In this embodiment, the use is preferably for improving short-time cognitive function, especially within 3 hours or within 2.5 hours after administration. Especially, cognitive function could be improved within a time span of 1 to 3 hours, more preferably within 1.5 to 2.5 hours after administration. It was found that especially executive function in the absence of fatigue can be improved.

In another embodiment of the invention, the inventive use is for decreasing psychomotor function of an animal, preferably a human, which is not experiencing fatigue. In this embodiment, the use is preferably for decreasing long-time psychomotor function, especially after more than 3 hours after administration. Preferably, psychomotor function is decreased within a time span of 3 to 8 hours, preferably within 3.5 to 6.5 hours, after administration. It was found that at the same time, higher cognitive processes, such as memory and executive function, are not impaired. This effect of carnitine may be advantageous for calming down or relaxing an individual. For example, this may be advantageous for individuals, who are nervous, irritable, hyperactive and/or suffering from attention deficit hyperactivity disorder (ADHD).

According to the invention, it is highly preferred to use L-carnitine or a salt of L-carnitine.

Preferably, the salt of L-carnitine or salt of a derivative of L-carnitine is a salt of a carboxylic acid, such as a tartrate, citrate, succinate, fumarate or hydrochloride. In a preferred embodiment of the invention, L-carnitine tartrate or L-carnitine citrate is used.

According to the invention, a salt of L-carnitine, a derivative of L-carnitine and/or a salt of a derivative of L-carnitine can be used. Under physiological conditions, the derivative should be converted into L-carnitine. Preferably, the derivative is a derivative of L-carnitine, in which the hydroxyl group is substituted with a substituent which is cleaved of under physiological conditions. The derivative of L-carnitine may be acetyl-L-carnitine, which is known to be converted into L-carnitine under physiological conditions. However, according to the invention, it was found that the beneficial effect of L-carnitine is pronounced, whereas preliminary findings suggest that the effect of acetyl-L-carnitine is at best moderate.

In another embodiment of the invention, the salt of a derivative of carnitine is an amino carnitine. Amino carnitines are inner salts of L-carnitinyl esters, especially inner salts of acetyl-L-carnitine or propionyl-L-carnitine. Preferably, the amino carnitine is an inner salt of an L-carnitine ester, an amino acid and at least one anion or acid, preferably chloride or hydrochloric acid. Preferably, the amino carnitine is selected from glycine propionyl L-carnitine hydrochloride, acetyl-L-carnitine arginate dihydrochloride or taurine acetyl-L-carnitine hydrochloride.

The dosage is selected depending on the purpose of administration, the animal to whom it is administered (sex, age, body weight, etc.) and similar factors. In a preferred embodiment of the invention, the L-carnitine, salt or derivative thereof is administered in an amount between 10 and 3000 mg, more preferably 100 to 1500 mg, most preferably between 250 to 1000 mg.

Preferably, the L-carnitine, salt of L-carnitine, derivative of L-carnitine and/or salt of a derivative of L-carnitine is administered in an amount corresponding to an equivalent amount of L-carnitine between 10 and 3000 mg, preferably between 50 and 1900 mg, more preferably between 100 and 1500 mg or between 250 and 750 mg. The equivalent amount of L-carnitine in an L-carnitine salt is the total amount of L-carnitine in the salt. The equivalent amount if L-carnitine in a derivative or salt thereof is the total amount of L-carnitine after cleaving of the substituent or substituents. It was found that an amount or equivalent amount of 500 mg L-carnitine is especially beneficial.

In a preferred embodiment of the invention, the L-carnitine, salt or derivative thereof is administered in a single dose. This is advantageous, because complicated dosage instructions are not necessary. However, the carnitine, salt or derivative thereof could also be administered in multiple doses.

Preferably, the use is not a long-term use. The use should rather be in response to a temporary event of fatigue and/or decreased cognitive function. Preferably, the use is not a long-term treatment over a time period of for more than one day, or even weeks or months. Nonetheless, the L-carnitine may be administered in response to multiple outbreaks of fatigue or cognitive problems within a relatively short time period.

In a preferred embodiment of the invention, the L-carnitine, salt or derivative thereof is administered in pure form. In another preferred embodiment, it is used as part of a composition comprising more than 50%, more than 80% or more than 95% (w/w) L-carnitine, based on the total weight of the composition.

Preferably, the L-carnitine, salt or derivative thereof is the main active ingredient in the composition. In this embodiment, it is preferred that the composition comprises more than 50%, more than 80% or more than 95% (w/w) L-carnitine, based on the total amount of all active ingredients. Active ingredients are usually vitamins, antioxidants etc. Non-active ingredients are solvents, carriers and the like.

In a preferred embodiment of the invention, the L-carnitine, salt or derivative thereof is not administered in combination with another agent which is effective in reducing or preventing fatigue or for improving cognitive functions in an animal.

Preferably, the carnitine, derivative or salt is not administered in combination with vitamins, especially vitamin E, or coenzyme Q10, and/or with organic acids, such as maleic acid, biotin or pantothenic acid.

In a preferred embodiment of the invention, the L-carnitine, salt or derivative is administered orally, preferably in the form of a liquid or a solid preparation, such as a tablet, capsule, powder, or a gel or a paste. The dosage form is selected in view of the route of administration. Examples of oral preparations include powders, granules, tablets, capsules, pills, inhalers, enteric coated preparations, liquids for internal use, suspensions, emulsions and syrups. To prepare these dosage forms, auxiliary substances commonly used in the field of pharmaceutical manufacturing technology, such as excipients, binders, antiseptics, antioxidants, disintegrators, lubricants, and flavoring agents, can be used as necessary. From the above, a tablet, powder or solution is preferred. The L-carnitine, salt or derivative may also be provided as an effervescent tablet or powder or the like for preparing a liquid preparation.

In another embodiment of the invention, the L-carnitine, salt or derivative is administered as part of a food and drink. Preferably, the food or drink is a functional food or drink. Preferred drinks are energy drinks or shots. The use may also be as a nutritional supplement. It may be used in conjunction with common additives for food products, such as sweeteners, seasonings, antiseptics, preservatives, germicides and antioxidants. In a preferred embodiment, the drink or food comprises the desired dose for a single administration.

Preferably, the composition comprises at least one carrier. The L-carnitine, salt or derivative may also be used in a combination, consisting essentially of the L-carnitine, salt or derivative and at least one carrier. Preferably, the carrier is selected from cellulose or microcrystalline cellulose and cellulose derivatives like HPMC, HPC and ethylcellulose, starch and modified starch, Ca-carbonates and Ca-silicates, lactose, sugars or sugar alcohols and derivatives and edible wax.

It is preferred that the animal is human. However, the animal may also be a non-human mammal. The animal may be any animal known to have relatively highly developed cognitive abilities. In a preferred embodiment, the animal is a horse or a pet, preferably a dog or cat. Dogs have highly developed cognitive abilities, especially dogs assisting humans, for example as police dogs, guide dogs, rescue dogs, herd dogs or hunting dogs.

Another subject of the invention is a non-therapeutic method for reducing or preventing fatigue and/or for improving cognitive function in an animal, comprising administering L-carnitine, salt of L-carnitine, a derivative of L-carnitine and/or salt of a derivative of L-carnitine to that animal.

Another subject of the invention is also a non-therapeutic composition for reducing or preventing fatigue and/or for improving cognitive function in an animal, the composition comprising L-carnitine, a salt of L-carnitine, a derivative of L-carnitine and/or salt of a derivative of L-carnitine.

The method of the invention is carried out, and the composition of the invention is prepared fully in accordance with the above described use of the invention. In other words, all the specific embodiments of the use of the invention disclosed herein are also specific embodiments of the method and composition of the invention.

The inventive use, method and composition solve the problem underlying the invention. Surprisingly, it was found that L-carnitine is an efficient agent for reducing or preventing fatigue and improving cognitive functions in an animal, especially in humans, especially in young and healthy individuals. In the prior art, similar functions of L-carnitine were only attributed to the treatment of individuals suffering from diseases associated with disturbed metabolism, or elderly subjects with impaired carnitine metabolism or athletes recovering from extreme exercise. Further compositions, such as energy drinks or functional foods or specific mixtures of L-carnitine with other vitamins are known in the art. However, an impact of L-carnitine against fatigue or for improving cognitive function has never been attributed specifically to L-carnitine itself. It was not known previously that L-carnitine would be useful by itself, if not being part of a multi-component composition. The inventive use, method and composition are easily applicable and available, especially when using a single dose. According to the invention, individuals experiencing temporary fatigue or impairment of cognitive function, such as students or truck drivers, can overcome this impairment rapidly and in a simple way without risks or side effects.

FIGURES

FIG. 1 shows a timeline and running order for each assessment. Participants arrived at 8.30 am on each occasion and consumed a standard breakfast. Following the baseline completion of the attention tasks and two 10 minute repetitions of the CDB battery tasks they received the day's treatment (placebo, 500 mg LC, 2000 mg LC, 1000 mg ALC). Two hours later they completed the attention tasks, the CDB (6 repetitions) and the executive tasks with mood assessments as shown.

Figure 2:
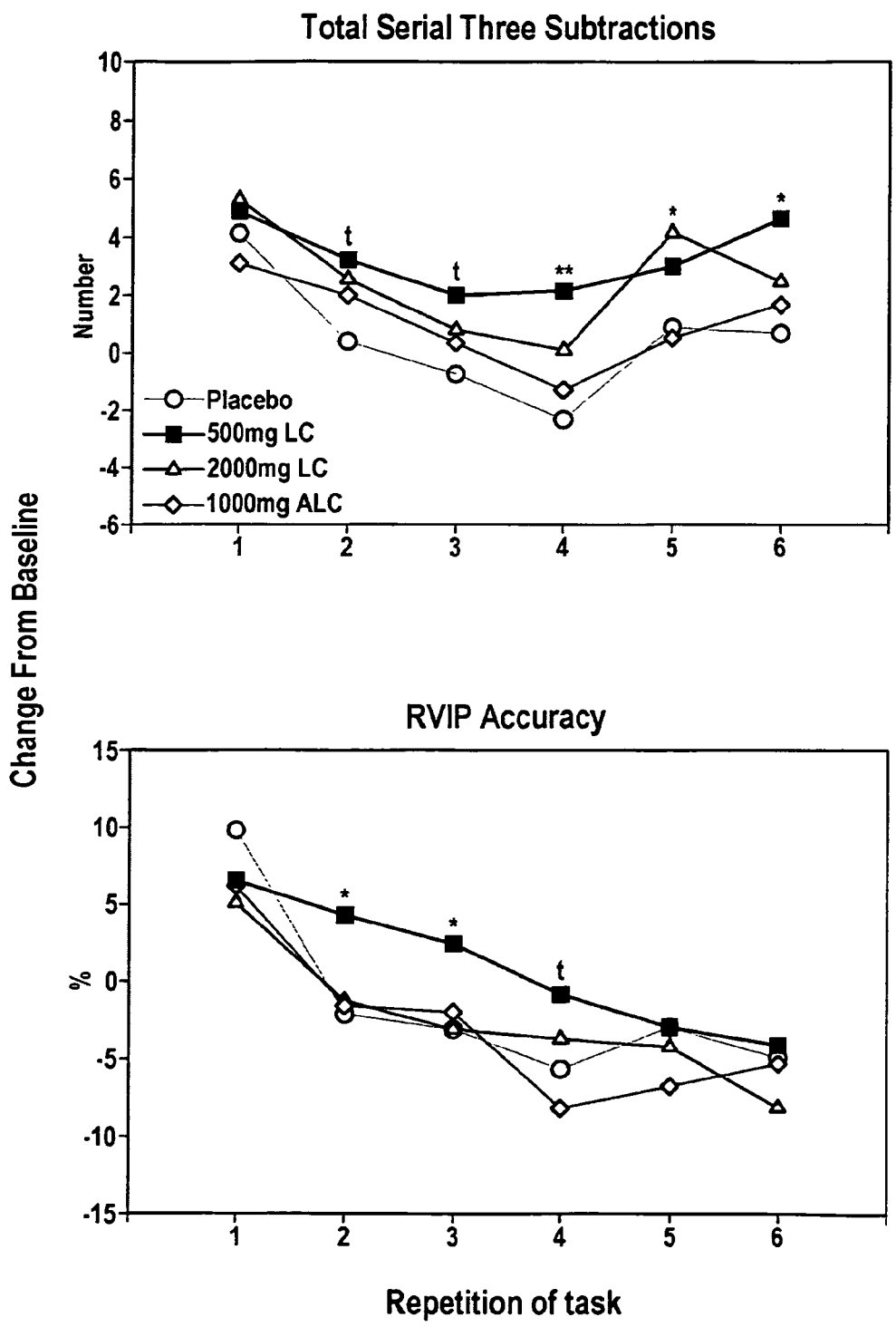
Figure 2:
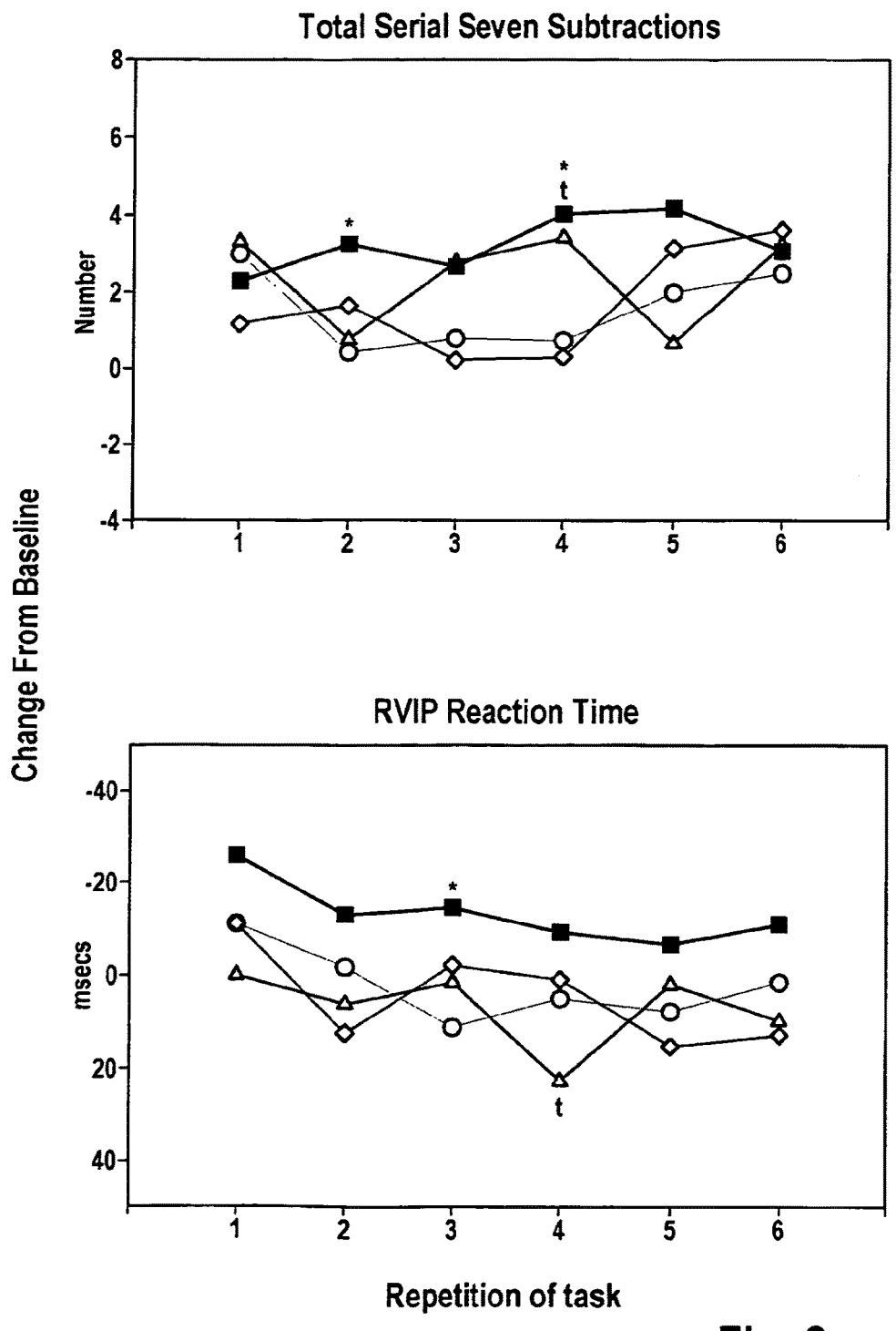

FIG. 2 shows the mean 'change from baseline' scores for each treatment on outcomes from the CDB. Significant treatment effects on the planned comparisons comparing each treatment with placebo on data from each repetition of the battery are indicated (t=trend; *$p<0.05$; **$p<0.01$). Graphs are plotted with up indicating benefits.

Figure 3:
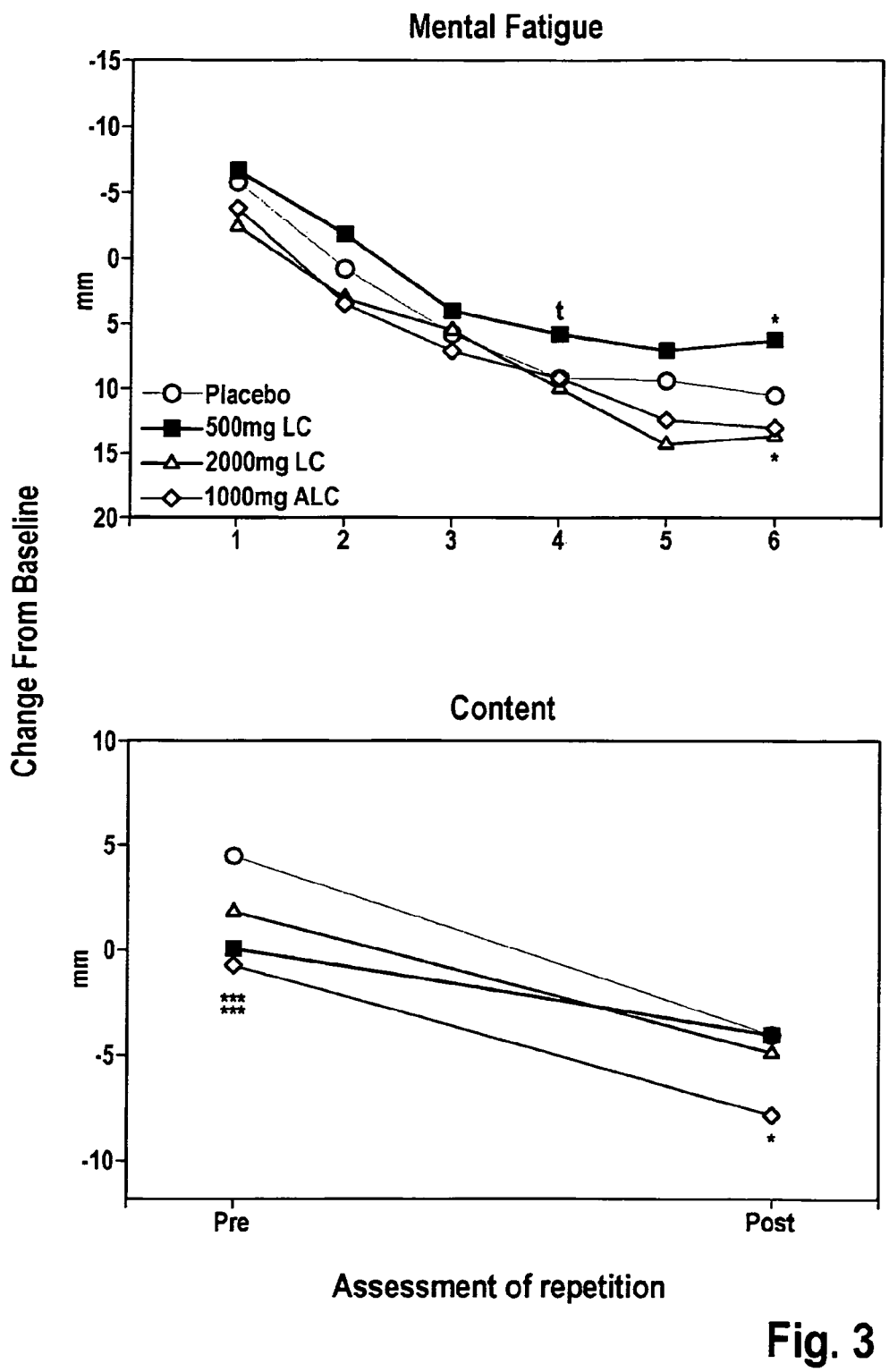
Figure 3:
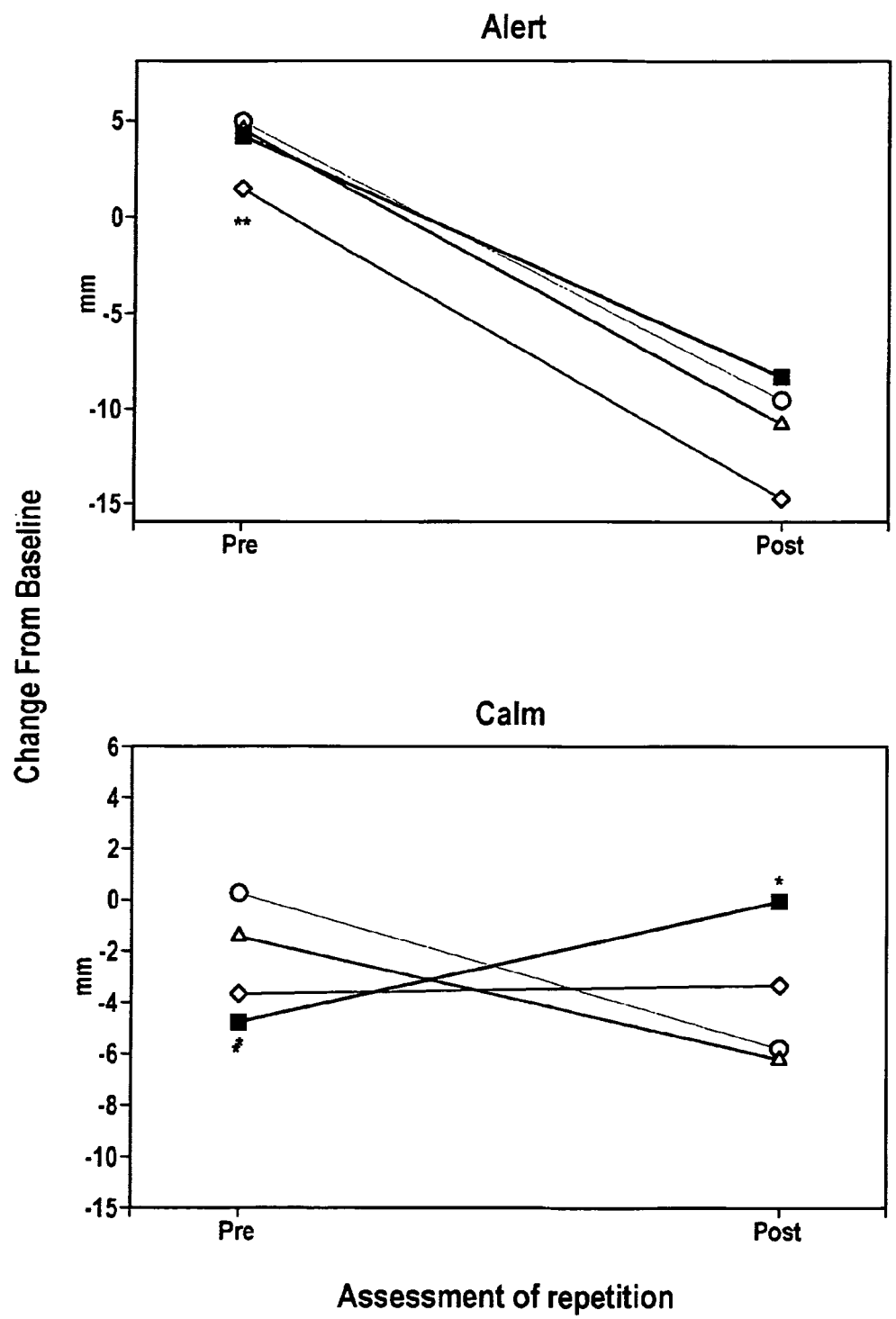

FIG. 3 shows the mean change from baseline ratings for each treatment of mental fatigue across the 6 repetition of the CDB and alert, content and calm ratings assessed pre and post-task performance. Significant treatment effects compared with placebo are indicated (t=trend; *$p<0.05$; **$p<0.01$). Graphs are plotted with up indicating benefits.

FIG. 4: The table shows mean (plus Standard Errors of Means) pre-dose baseline scores and post-dose 'change from baseline' scores, plus F and P statistics from the ANOVAs, for the cognitive tasks that were completed once pre-dose and once post-dose.

FIGS. 5a, 5b: The tables show mean (plus Standard Errors of Means) pre-dose baseline scores and post-dose 'change from baseline' scores, plus F and P statistics from the ANOVAs (T=treatment main effect, T×R=treatment×repetition interaction), for the baseline and six post-dose repetitions of the CDB tasks.

FIG. 6: The table shows mean (plus Standard Errors of Means) pre-dose baseline scores and post-dose 'change from baseline' scores, plus F and P statistics from the ANOVAs (T=treatment main effect, T×R=treatment×repetition interaction), for the baseline and two post-dose Bond-Lader assessments.

EXAMPLES

A. Cognitive Demand Battery (CDB)

The study described in the following utilized a computerized Cognitive Demand Battery (CDB) that has been shown to be sensitive to cognitive enhancement inculcated by a number of natural food components and supplements (Kennedy et al. 2008; Kennedy and Scholey 2004; Reay et al. 2005; 2006). The working hypothesis underlying this approach is that neural activity is costly in terms of local neural resources (e.g. metabolic substrates) and that the brain is therefore liable to suffer deficiencies in the short term. Any psychoactive properties of a test substance are therefore liable to be more readily apparent during this period of intense cognitive demand and the 'mental fatigue' state elicited by prolonged task performance. This paradigm may therefore be more sensitive than the use of less demanding cognitive tasks, particularly if an intervention has an impact on the delivery or utilisation of metabolic substrates.

Additionally, the methodology took advantage of the intrinsic relationship between fatigue and aspects of cognitive function. As an example, the speed of performing tasks assessing attention is related to both sleep deprivation and sleep duration. Similarly, mental fatigue has been shown to impact negatively on a wide variety of cognitive tasks, with the effects most pronounced for those tasks that require high levels of executive control of cognitive processes, i.e. the brain function that controls and manages other cognitive processes, and which is intrinsic to processes such as planning, cognitive flexibility, rule acquisition, abstract thinking, and inhibiting irrelevant sensory information and inappropriate actions (Kato et al. 2009; Lorist et al. 2009). Previous research has established that fatigue related deficits in both cerebro-electrical activity and tasks requiring executive control processes can be inculcated by extended 'difficult' task performance in the laboratory (Boksem et al. 2005, van der Linden 2003). The proposed methodology will take advantage of the potential performance decrements related to the mental fatigue associated with task performance by interposing two executive function tasks after the 60 minutes of the CDB.

In the current double-blind, placebo-controlled, balanced cross-over experiment we assessed the effects of single doses of LC (500 mg and 2000 mg) and ALC (1000 mg), administered on separate occasions, on mental fatigue and cognitive function during extended performance of mentally demanding tasks in healthy, young male and female adults.

Materials and Methods

Design

This study employed a randomized, double-blind, placebo-controlled, balanced cross-over design.

Participants 20 healthy adults (10 male, 10 female, 18 to 25 years) who had not taken prescription or illicit drugs or any food supplements within the preceding 4 weeks were recruited. Smokers and excessive consumers of caffeine were excluded, as were those who had consumed alcohol or caffeine within the 12 hours prior to a testing session.

Treatments

Each participant received each treatment in an order counterbalanced by random allocation to a Latin square. Depending on the condition to which the participant was allocated on each day they received 4 capsules containing either 500 mg LC or 500 mg ALC or a placebo which were combined to give a total dose of either:

1) Placebo
2) 500 mg L-carnitine (LC; as 750 mg Carnipure™ tartrate, Lonza AG)
3) 2000 mg L-carnitine (LC; as 3000 mg Carnipure™ tartrate, Lonza AG)
4) 1000 mg acetyl-L-carnitine (ALC; as Carnipure™ ALC, Lonza AG)

Cognitive and Mood Measures

Prior to the Cognitive Demand Battery (CDB) three tasks assessed simple psychomotor function and attention.

Simple Reaction Time

The participant pressed the response button as quickly as possible every time an upwards pointing arrow appeared on screen. Fifty stimuli were presented with an inter-stimulus duration that varied randomly between 1 and 3.5 seconds. The outcome was speed of response (msecs).

Choice Reaction Time

Arrows pointing to the left or to the right were presented on the screen, one at a time. Participants respond by pressing a left or right key press corresponding to the direction of the arrow. Fifty stimuli were presented with an inter-stimulus duration that varied randomly between 1 and 3.5 seconds. The outcomes were speed of response (msecs) and accuracy (% correct).

Four Choice Reaction Time

A visual representation of arrows, pointing up, down, left and right was presented on screen. The arrows 'lit up' at random with participants responding with the corresponding response button. A total of 48 stimuli were presented with an inter-stimulus duration that varied randomly between 1 and 3.5 seconds. The outcomes were speed of response (msecs) and accuracy (% correct).

Cognitive Demand Battery (CDB)

The objective of this battery is to assess the impact of a treatment on speed/accuracy and mental fatigue during continuous performance of cognitively demanding tasks. Application of this battery in its 60 minute form (i.e. 6 repetitions of the 10-minute battery) has been shown to reliably increase self-ratings of 'mental fatigue' and to be sensitive to a number of herbal and natural interventions (Kennedy et al. 2008; Kennedy and Scholey 2004; Reay et al. 2005; 2006). The 10 minute battery comprises:

Serial Subtractions (3s and 7s—Two Minutes Each)

Modified, two minute, computerised versions of the Serial Threes and Serial Sevens tests were utilised. For both tasks a standard instruction screen informed the participant to count backwards in threes or sevens from the given randomly generated number, as quickly and accurately as possible, using the linear number keys to enter each response. Participants were also instructed verbally that if they made a mistake they should continue subtracting from the new, incorrect number. Each three-digit response was entered using the linear number keys on the keyboard with each digit being represented on screen by an asterisk. Pressing the enter key signals the end of each response and clears the three asterisks from the screen. The task was scored for total number of subtractions and number of errors. In the case of incorrect responses, subsequent responses were scored as positive if they were correct in relation to the new number.

Rapid Visual Information Processing Task (5 Minutes)

The participants monitored a continuous series of digits for targets of three consecutive odd or three consecutive even digits. The digits were presented at the rate of 100 per minute and the participants responded to the detection of a target string by pressing a response key as quickly as possible. The task is continuous and lasts for 5 minutes, with 8 correct target strings being presented in each minute. The task was scored for percentage of target strings correctly detected, average reaction time for correct detections, and number of false alarms.

Subjective 'Mental Fatigue' Scale

At the end of each set of tasks participants were asked to indicate how mentally fatigued they felt by marking a 100 mm line with the end-points labelled "not at all" and "extremely".

Executive Function Tasks

It has been hypothesised (see above) that cognitive deficits due to mental fatigue reflect decrements in executive functioning. The following classic 'executive' tasks have been shown to be sensitive to fatigue (van der Linden et al. 2003).

Logical Reasoning Task

Participants were required to decide whether a series of statement correctly described the order of 2 letters. They were shown a number of short sentences each followed by a pair of letters. The sentences claimed to describe the order of the two letters, i.e., to say which came first. They could do this in several different ways. For example, the order AB can be correctly described by saying either (1) A precedes B or (2) B follows A, or (3) B does not precede A, or (4) A does not follow B. All these are correct descriptions of the pair AB but are incorrect when applied to the other pair BA. Participants were required to decide whether each sentence was a true or false description of the letter pair which followed it. The task was scored for accuracy and response times.

Stroop Task

This is a computerised version of a commonly used classic task which requires attentional and central executive resources. In this case the task ran for 10 minutes, with the data collapsed into 2 minute epochs. Words describing one of four colours ('RED', 'YELLOW', 'GREEN', 'BLUE') were presented in different coloured fonts in the centre of a computer screen. The participants pressed one of four coloured response buttons in order to identify the font colour (e.g. if the word 'GREEN' was presented in a blue font, the correct response would be to respond with the blue button). The presented words were either 'congruent' (word and font are the same colour) or 'incongruent' (word and font are different colours) and were presented in a random order. The task was scored for reaction times and accuracy of responses to 'congruent' and 'incongruent' words.

Mood

Bond-Lader Mood Scales (Bond and Lader 1974)

Prior to and following the tasks mood was assessed with Bond and Lader scales. This measure has been utilised in numerous pharmacological, psychopharmacological and medical trials. The scales comprise a total of sixteen lines (approximately 100 mm on screen) anchored at either end by antonyms (e.g. alert-drowsy, calm-excited). Subjects indicate their current subjective position between the antonyms on the line. Individual item scores were calculated as % distance along the line. Outcomes comprised three factor analysis derived scores: 'Alertness', 'Calmness' and 'Contentment'.

Procedure

Participants attended the laboratory on five separate occasions. Testing took place in a suite of testing facilities with participants visually isolated from each other.

The first, introductory visit to the laboratory comprised: obtaining of informed consent; training on the cognitive and mood measures; health screening; and collection of demographic data.

Following the introductory visit participants attended the laboratory at 8.30 am on four further occasions, one week apart, receiving a different treatment on each occasion. They fasted (no food or drink except for water) and consumed no caffeine or alcohol for at least 12 hours prior to each session. On their first study day participants were randomly allocated to a treatment regime on the Latin square. On arrival on each occasion participants consumed a standard breakfast (40 g Kellogg's All-bran with 150 ml skimmed milk and a glass of water) following which they undertook an initial cognitive/mood assessment comprising completion of the attention tasks ('Simple'/'Choice'/'Four choice' reaction time) followed by 2 completions of the 10 minute CDB tasks (the first completion was a practice and the second was used for baseline assessment of performance) and the Stroop and Logical Reasoning tasks. They then consumed their treatment for that day. At 120 minutes post-dose they completed the attention tasks then commenced the full 60 minute (i.e. 6 completions of the 10 minutes of tasks) CDB. Following completion of the CDB participants completed the 'Logical Reasoning' and the 'Stroop' executive function tasks. Mood was assessed with Bond-Lader mood scales pre-treatment and before and after the post-treatment cognitive assessment. The set-up is shown schematically in FIG. 1.

Statistical Approach

Primary Analysis

Statistical analysis for all of the cognitive/fatigue and mood measures derived from the battery were analysed by repeated measures Analysis of Variance (ANOVA) of baseline adjusted data (calculated against pre-dose). Measures with a single post-dose repetition (attention tasks, executive tasks) were analysed by one way ANOVA (condition). Measures with multiple post-dose repetitions (Mood, CDB) were analysed with two way ANOVA (condition×repetition). Planned comparisons (placebo versus each active treatment) were then undertaken on baseline adjusted data from the single completion, or each of the multiple completions, as appropriate, utilising t-tests with Mean Squares Error from the ANOVA (Keppel 1991).

Results

The statistics from the ANOVAs are shown in FIGS. 4, 5 and 6.

Cognitive Tasks

Reaction Time Tasks

Neither the initial ANOVAs nor planned comparisons revealed any significant effects on the Simple Reaction Time, Choice Reaction Time or 4-Choice Reaction Time tasks.

Executive Tasks

Neither the initial ANOVAs nor planned comparisons revealed any significant effects on the Stroop task or Logical reasoning task.

Cognitive Demand Battery (CDB)

FIG. 2 shows the outcomes from the CDB that evinced significant effects on the planned comparisons of data from each active treatment to placebo during each repetition of the tasks.

Serial Subtractions

Serial 3s: The initial ANOVA showed no significant main effect of condition or interaction involving condition on performance of the Serial 3s task. However, the planned comparisons showed that participants carried out more subtractions following 500 mg LC compared to placebo during the 4th [$t$ [270]=2.74, $p$=0.006] and 6th [$t$ [270]=2.41, $p$=0.016] repetitions, with statistical trends towards the same effect during the 2nd [$t$ [270]=1.74, $p$=0.08] and 3rd [$t$ [270]=1.67, $p$=0.09] repetitions. In addition, more subtractions were made during the 5th repetition following 2000 mg of LC compared to placebo [$t$ [270]=2.06, $p$=0.04]. This latter effect is not replicated at other repetitions so may be attributable to a type 1 error. There was no significant effect on the accuracy (number of errors) of performance.

Serial 7s: The initial ANOVA showed no significant main effects or interactions involving treatment on the serial 7s task. However, the planned comparisons showed that participants completed more subtractions following 500 mg compared to placebo during the 2nd [$t$ [255]=2.02, $p$=0.044] and 4th [$t$ [255]=2.38, $p$=0.018] repetitions. There was also a trend towards more subtractions following 2000 mg LC compared to placebo during the 4th repetition [$t$ [255]=1.94, $p$=0.053]. There was no significant effect on the accuracy (number of errors) of performance.

RVIP

ANOVA revealed a main effect of condition on speed of responses on the RVIP task [$F(3,57)$=2.78, $p<0.05$]. However, post-hoc comparisons of the treatment means showed that this effect was due to differences between active treatments, rather than with placebo. The planned comparisons also revealed that, whilst participants performed faster at each repetition following 500 mg LC, this effect only reached significance during the 3rd repetition of the task [$t$ [285]=2.51, $p$=0.013]. There was also a trend towards slower responding following 2000 mg LC during the 4th repetition [$t$ [255]=1.71, $p$=0.089].

Whilst the initial ANOVA showed no significant main effect of condition or interaction involving condition on the accuracy of performing the RVIP task, the planned comparisons showed that 500 mg LC outperformed placebo during the 2nd [$t$ [285]=2.44, $p$=0.015] and 3rd [$t$ [285]=2.11, $p$=0.036] repetitions of the task, with a trend towards the same effect during the 4th [$t$ [285]=1.83, $p$=0.07] repetition.

Subjective Fatigue

As expected the ANOVA revealed a main effect of repetition [$F(5,95)$=42.32, $p<0.001$] with increasing fatigue throughout the repetitions of the tasks. However, there was no main effect of condition or a condition by repetition interaction. The planned comparisons did reveal that ratings of fatigue were lower following 500 mg LC compared to placebo during the 6th repetition [$t$ [285]=2.14, $p$=0.033] with a trend towards the same effect during the 4th repetition [$t$ [285]=1.85, $p$=0.065]. In contrast fatigue ratings were higher than placebo following 2000 mg LC following the 5th repetition [$t$ [285]=2.32, $p$=0.02].

Bond-Lader Mood Scales

The results are shown in FIG. 3. The initial ANOVA showed no significant treatment related effects on the Bond-Lader mood scales. However, following 500 mg LC participants rated themselves as less calm [$t$ [57]=2.12, $p$=0.037] and less content [$t$ [57]=3, $p$=0.004] at the first (pre-task) assessment, with this effect dissipating by the post task assessment, at which point this group rated themselves as more calm [$t$ [57]=2.47, $p$=0.016]. Following 1000 mg ALC participants rated themselves as less alert before undertaking the tasks [$t$ [57]=2.7, $p$=0.009] and less content both before [$t$ [57]=3.6, $p$=0.001] and after [$t$ [57]=2.5, $p$=0.015] the post-dose tasks.

Summary of Findings

The study employed two statistical analyses that were carried out independently of each other; focussed planned comparisons (t tests utilising Mean Squares Error from the ANOVA) that assessed any differences between placebo and each of the three active treatment at each assessment, and a more general ANOVA that assessed main effects and interaction effects (where appropriate) across treatments and assessments. There were no significant differences in the second of these analysis (ANOVA), but there was a pattern of effects evident within the planned comparisons. The following summarizes the effects evident for each of the treatments in comparison to placebo.

500 mg LC (as 750 mg Carnipure Tartrate)

Significant benefits on the planned comparison analyses were seen in performance of each of the CDB tasks. Participants completed more Serial 3 subtractions during two repetitions, with trends towards improvements at a further two time-points. They also completed more Serial 7 subtractions at two time points, and responded more quickly on the RVIP task during one repetition of the task. This latter effect was accompanied by improved accuracy on the RVIP at two time-points, with a trend towards an improvement during one further repetition. Participants in this condition also reported themselves as numerically less 'mentally fatigued' after each repetition of the tasks, but this effect only reached significance after the last set of tasks, with a trend towards the same effect at one other time-point.

Results in terms of mood on the Bond-Lader scales were mixed, with 500 mg LC associated with reduced 'calmness' and 'contentment' before starting the post-treatment tasks, but increased 'calmness' following completion of the assessment.

2000 mg LC (as 3000 mg Carnipure Tartrate)

The pattern with regards 2000 mg LC was composed of several isolated differences. Participants completed more Serial 3s at one time point, with a trend towards increased Serial 7s subtractions at one time-point. In contrast there was a trend towards slower responses on the RVIP and significantly increased ratings of mental fatigue at one repetition. Given that the pattern of results is composed of single, contradictory findings it seems likely that the results pertaining to this treatment are due to chance.

1000 mg ALC (as Carnipure ALC)

ALC was associated with negative effects on mood with lower levels of alertness at the second post-dose time-point and reduced levels of 'contentment' at both post-dose time points.

Conclusion

Despite a lack of any significant treatment related effects on the ANOVAs there was consistent evidence of significant improvements in performance of the CDB following 500 mg LC in comparison to placebo on the planned comparisons. However, there was no evidence of benefits following the 2000 mg LC and 1000 mg ALC treatments.

Discussion

The findings from the current study demonstrate that 500 mg LC enhance the cognitive performance of healthy, young adults. Improvements were seen during more than one (of six) task repetition on all three of the Cognitive Demand Battery tasks, with some evidence of a treatment related attenuation of task related mental fatigue. Presently, there was no consistent evidence that the higher dose (2000 mg) of LC or 1000 mg ALC had beneficial effects.

B. Early Phase Cognitive Test Battery

Effects of carnitine on cognitive function were studied with a CogState™ 12 minute Early Phase cognitive test battery. The test was developed by CogState, US, and is described in U.S. Pat. No. 7,163,513 B2. The test uses playing cards and computer mazes for measuring the cognitive domains of executive function, psychomotor function, visual attention and visual learning. Tasks correspond to cognitive domains as follows:

Maze learning task. Executive function/spatial problem solving

Detection task: Psychomotor function/speed of processing

Identification task: Visual attention/vigilance

One card learning task: Visual learning

The test is designed such that the individuals do not experience fatigue when performing the tests. It was carried out with 20 healthy male and female individuals aged between 20 and 40 years. The test was double-blind and placebo-controlled and studied effects of 500 mg L-carnitine, administered as 736 mg L-carnitine L-tartrate (Carnipure™ tartrate, Lonza AG) in water in a single dose. A single test battery of about 10 min comprised maze learning task, a detection task with playing cards, an identification task with playing cards and a one card learning task. Consecutive accomplishing of the test battery took place twice prior to and hourly after intake of the study preparation over a period of 6 hours.

Comparison and evaluation of the results showed, that there is some evidence for a short-acting benefit of L-carnitine on executive function two hours after sample intake. However, there was no significant effect on visual attentional function or visual learning. Interestingly, a decrease of psychomotor function was observed after four, five and six hours. It was found that at the same time, higher cognitive processes, such as memory and executive function, are not impaired.

The results suggest that healthy individuals without fatigue may benefit from L-carnitine intake within a short interval of approximately two hours, whereas a long time improvement of cognitive function was not observed. The result complements the Cognitive Demand Battery (CDB) described above by suggesting an effect of carnitine administration on cognitive functions of individuals, who do not experience fatigue.

REFERENCES

Boksem M A S, Meijman T F, Lorist M M (2005) Effects of mental fatigue on attention: An ERP study. Cognitive Brain Research 25: 107-116

Cruciani R A, Dvorkin E, Homel P, Malamud S, Culliney B, Lapin J, Portenoy R K, Esteban-Cruciani N (2006) Safety, Tolerability and Symptom Outcomes Associated with I-Carnitine Supplementation in Patients with Cancer, Fatigue, and Carnitine Deficiency: A Phase I/II Study. Journal of Pain and Symptom Management 32: 551-559

Karlic, H., Lohninger, A., (2004) Supplementation of L-carnitine in athletes: does it make sense? Nutrition 20:709-715

Kato Y, Endo H, Kizuka T (2009) Mental fatigue and impaired response processes: Event-related brain potentials in a Go/NoGo task. International Journal of Psychophysiology 72: 204-211

Kennedy D O, Haskell C F, Robertson B, Reay J, Brewster-Maund C, Luedemann J, Maggini S, Ruf M, Zangara A, Scholey A B (2008) Improved cognitive performance and mental fatigue following a multi-vitamin and mineral supplement with added guarana (Paullinia cupana). Appetite 50: 506-513

Kennedy D O, Scholey A B (2004) A glucose-caffeine 'energy drink' ameliorates subjective and performance deficits during prolonged cognitive demand. Appetite 42: 331-333

Kennedy D O, Dodd F L, Okello E J, Reay J L, Scholey A B, Haskell C F (2010) Monoterpenoid extract of sage with cholinesterase inhibiting properties improves cognitive performance and mood in healthy adults. J. Psychopharmacol. October 2011 (Epub. ahead of print).

Lorist M M, Bezdan E, ten Caat M, Span M M, Roerdink J B T M, Maurits N M (2009) The influence of mental fatigue and motivation on neural network dynamics; an EEG coherence study. Brain Research 1270: 95-106

Malaguarnera M, Cammalleri L, Gargante M P, Vacante M, Colonna V, Motta M (2007) L-Carnitine treatment reduces severity of physical and mental fatigue and increases cognitive functions in centenarians: a randomized and controlled clinical trial. American Journal of Clinical Nutrition 86: 1738-1744

Malaguarnera M, Gargante M P, Cristaldi E, Colonna V, Messano M, Koverech A, Neri S, Vacante M, Cammalleri L, Motta M (2008) Acetyl L-carnitine (ALC) treatment in elderly patients with fatigue. Archives of Gerontology and Geriatrics 46: 181-190

Montgomery S A, Thal L J, Amrein R (2003) Meta-analysis of double blind randomized controlled clinical trials of acetyl-L-carnitine versus placebo in the treatment of mild cognitive impairment and mild Alzheimer's disease. International Clinical Psychopharmacology 18: 61-71

Reay J L, Kennedy D O, Scholey A B (2005) Single doses of Panax ginseng (G115) reduce blood glucose levels and improve cognitive performance during sustained mental activity. Journal of Psychopharmacology 19: 357-365

Reay J L, Kennedy D O, Scholey A B (2006) Effects of Panax ginseng, consumed with and without glucose, on blood glucose levels and cognitive performance during sustained mentally demanding tasks. J. Psychopharmacol. 20, 771-81.

van der Linden D, Frese M, Meijman T F (2003) Mental fatigue and the control of cognitive processes: effects on perseveration and planning. Acta Psychologica 113: 45-65

The invention claimed is:

1. A non-therapeutic method for reducing or preventing mental fatigue and/or for improving cognitive function of a healthy non-elderly individual having an age of from about 16 to about 50 years of age, wherein the mental fatigue and/or impaired cognitive function that is prevented or improved is not the result of a disease or due to old age, the method comprising administering an amount of L-carnitine, and/or a salt of L-carnitine corresponding to an equivalent amount of L-carnitine of from about 100 mg to about 1500 mg to the individual in a single dose over a time period of not more than one day, wherein the L-carnitine, and/or a salt of L-carnitine, is not administered in combination with another agent which is effective in reducing or preventing fatigue or for improving cognitive function of the individual.

2. The method of claim 1, wherein the animal is human.

3. The method of claim 1, wherein the animal does not suffer from chronic L-carnitine deficiency.

4. The method of claim 1, wherein before administration of the L-carnitine, and/or salt of L-carnitine, the animal is experiencing a temporary fatigue and/or temporary impairment of cognitive function.

5. The method of claim 1, wherein the salt is a tartrate, citrate, succinate, fumarate or hydrochloride.

6. The method of claim 1, wherein the L-carnitine, and/or salt of L-carnitine, is administered in an amount corresponding to an equivalent amount of L-carnitine between 250 and 1000 mg.

7. The method of claim 1, wherein the L-carnitine, and/or salt of L-carnitine, is administered as part of a solid composition comprising more than 50% (w/w) L-carnitine.

8. The method of claim 1, wherein the L-carnitine, and/or salt of L-carnitine, is administered orally.

9. The method of claim 1, wherein the animal is a horse or a pet.

10. A method for reducing or preventing mental fatigue and/or for improving cognitive function in a healthy non-elderly animal having an age of from about 16 to about 50 years of age, wherein the mental fatigue and/or impaired cognitive function that is prevented or improved is not the result of a disease or due to old age, comprising administering an amount of L-carnitine and/or a salt of L-carnitine corresponding to an equivalent amount of L-carnitine of from about 100 mg to about 1500 mg, to that animal, wherein the method is non-therapeutic, and wherein the L-carnitine and/or salt of L-carnitine is not administered over a time period of more than one day, and wherein the L-carnitine, and/or a salt of L-carnitine, is not administered in combination with another agent which is effective in reducing or preventing fatigue or for improving cognitive function of the individual.

11. The method of claim 6, wherein the L-carnitine, and/or salt of L-carnitine, is administered in an amount corresponding to an equivalent amount of L-carnitine between 250 and 1000 mg.

12. The method of claim 8, wherein the L-carnitine, and/or salt of L-carnitine, is administered in the form of a liquid, a solid preparation, a gel or a paste.

13. The method of claim 12, wherein the solid preparation is a tablet, capsule or powder.

14. The method of claim 10, wherein the L-carnitine and/or salt of L-carnitine is administered in response to multiple outbreaks of fatigue or cognitive problems within a relatively short time period.

15. The method for improving cognitive function of claim 10, wherein short time cognitive function is improved.

16. The method of claim 15, wherein the short time cognitive function is improved within a time span of 1 to 3 hours after administration.

17. The method of claim 1, wherein short time cognitive function is improved.

18. The method of claim 17, wherein the short time cognitive function is improved within a time span of 1 to 3 hours after administration.

* * * * *